United States Patent
Yu et al.

(10) Patent No.: US 12,409,144 B2
(45) Date of Patent: Sep. 9, 2025

(54) OXYGEN CAPSULE AS WELL AS PREPARATION METHOD AND APPLICATION THEREOF

(71) Applicant: Vitalbase Inc., Winooski, VT (US)

(72) Inventors: Yong Yu, Lenox, MA (US); Mengchun Yu, Lenox, MA (US)

(73) Assignee: Vitalbase Inc., Winooski, VT (US)

( * ) Notice: Subject to any disclaimer, the term of this patent is extended or adjusted under 35 U.S.C. 154(b) by 0 days.

(21) Appl. No.: 18/253,535

(22) PCT Filed: Aug. 30, 2022

(86) PCT No.: PCT/CN2022/115821
§ 371 (c)(1),
(2) Date: May 18, 2023

(87) PCT Pub. No.: WO2023/065833
PCT Pub. Date: Apr. 27, 2023

(65) Prior Publication Data
US 2024/0000715 A1    Jan. 4, 2024

(30) Foreign Application Priority Data
Oct. 19, 2021  (CN) .......................... 202111218716.5

(51) Int. Cl.
| | |
|---|---|
| *A61K 9/48* | (2006.01) |
| *A23L 33/16* | (2016.01) |
| *A23P 10/30* | (2016.01) |
| *A61K 33/00* | (2006.01) |

(52) U.S. Cl.
CPC ............ *A61K 9/4833* (2013.01); *A23L 33/16* (2016.08); *A23P 10/30* (2016.08); *A61K 9/4825* (2013.01); *A61K 33/00* (2013.01)

(58) Field of Classification Search
CPC ............................. A61K 9/4833; A61K 47/44
See application file for complete search history.

(56) References Cited

U.S. PATENT DOCUMENTS

| | | | |
|---|---|---|---|
| 2013/0071455 A1* | 3/2013 | Dardelle ................. | A23L 27/70 264/4.1 |
| 2017/0360058 A1 | 12/2017 | Windhab et al. | |

FOREIGN PATENT DOCUMENTS

| | | | | |
|---|---|---|---|---|
| CN | 102908334 | A | 2/2013 | |
| CN | 105977793 | A | 9/2016 | |
| CN | 108464505 | A * | 8/2018 | ............. A61K 47/44 |
| CN | 108539592 | B | 4/2020 | |
| CN | 111972664 | A | 11/2020 | |
| EP | 2151242 | A1 * | 2/2010 | ............. A61P 31/04 |
| JP | 200869078 | A | 3/2008 | |
| JP | 2008069078 | A * | 3/2008 | |
| KR | 960006935 | A * | 3/1996 | |
| KR | 19960006935 | A | 3/1996 | |
| KR | 1020090024547 | A | 3/2009 | |

OTHER PUBLICATIONS

CN-108464505-A (Google English Translation, Downloaded Jun. 2025) (Year: 2025).*
Food Nutrition, pp. 162-163, Citation content: Cocoa butter butter is also a common edible oil, 2020 (date on untranslated version of document).
Grain, Oil and Food Processing Technology, p. 14, Citation content: Cocoa butter is polycrystalline, and different crystal forms correspond to different melting points. The temperature regulating process can make the molten cocoa butter form a stable crystal structure of cocoa butter when it cools, 2017 (date on untranslated version of document).
Oxygen Therapy and Health, pp. 10-12, Citation content: Negative oxygen ions in the air are unstable and can easily lose an electron and become ozone. For ozone, it is extremely unstable at room temperature and can decompose into oxygen molecules and atoms at any time, 2006 (date on untranslated version of document).
Weiwei, Zhang; Science and Technology Daily/Jun. 29, 2012/ Edition 001; Oxygenated particles allow rabbits to survive for 15 minutes with respiratory arrest, Reporter Zhang Weiwei, Jun. 2012 (date on document).

* cited by examiner

*Primary Examiner* — Mark V Stevens
(74) *Attorney, Agent, or Firm* — DINSMORE & SHOHL LLP

(57) ABSTRACT

An oxygen capsule preparation method includes the following steps: performing three-stage separation on deodorized cocoa butter; then mixing negative oxygen ions with deodorized cocoa butter liquid obtained after the three-stage separation; storing ionic oxygen in the deodorized cocoa butter liquid; and finally filling the deodorized cocoa butter liquid treated by the negative oxygen ions into a capsule shell to be prepared into the capsule, thereby obtaining the oxygen capsule. The oxygen capsule provided by the present disclosure is high in oxygen content, has a good oxygen supplementation effect, and has a good prevention or treatment or adjuvant treatment effect on various chronic non-infectious diseases (such as hypertension, gout, gastric ulcer and anxiety disorder), systemic lupus erythematosus and altitude stress.

3 Claims, 3 Drawing Sheets

OXYGEN CAPSULE AS WELL AS PREPARATION METHOD AND APPLICATION THEREOF

CROSS-REFERENCE TO RELATED APPLICATIONS

This application is the U.S. National Stage of PCT/CN2022/115821 filed on Aug. 30, 2022, which claims priority to Chinese Patent Application 202111218716.5 filed on Oct. 19, 2021, the entire content of both are incorporated herein by reference in their entirety.

FIELD OF THE INVENTION

The present disclosure belongs to the field of medical technologies, and particularly relates to an oxygen capsule as well as a preparation method and application thereof.

BACKGROUND OF THE INVENTION

Water, nutrients (including protein, fat, carbohydrates, minerals and trace elements) and oxygen are three elements necessary for human cell viability. Mild hypoxia will cause rapid heartbeat and shortness of breath, and even is life-threatening. Studies have shown that brain tissue cells experience irreversible death after several minutes without oxygen. Cell hypoxia is a critical factor in many diseases such as cancers, and immunological and degenerative disorders as the dominant majority of bacteria, viruses and cancer cells that are harmful to the human body are 12 more viable under hypoxic conditions. The Nobel Prize in Physiology and Medicine in 2019 was awarded to three scientists who studied the mechanisms of oxygen perception in the human body, and they concluded that hypoxia-inducible factor (HiF) was a transcription factor for hypoxia-associated genes. The accumulation of HIF in cells can induce the growth of tumor blood vessels. Therefore, oxygen supplementation has a direct promotion effect on human health, and can effectively improve the body's immunity and self-healing capacities.

The primary way for the human body to absorb oxygen is through breathing, in which molecular oxygen ($O_2$) is converted into ionic oxygen (O) by combination reaction with iron in hemoglobin through pulmonary alveoli, and the oxygen is then transported throughout the body to all organs through a blood circulation system. In order to save lives of patients, or for the purpose of maintaining health and delaying aging for sub-healthy people, various methods of artificial oxygen supplementation are constantly explored, commonly including oxygen inhalation, intubation, ventilators, hyperbaric oxygen chambers, etc. However, all these methods have to involve gas exchange through a human lung, which serves as an oxygen supply channel. In a case of a disorder in this oxygen supply channel, such as inhalation injuries caused by acute pneumonia, pulmonary edema and burns, and respiratory failure caused by brain injury, these commonly used respiratory tract oxygen-supplying methods are ineffective. As a result, a patient's life was seriously in danger. The development of new oxygen supply channels has emerged as a hot and challenging research topic.

Researchers at Boston Children's Hospital in the United States keep rabbits with blocked windpipes alive for 15 minutes without breathing while maintaining normal blood pressures and heart rates by injecting oxygen-filled microparticles into the rabbits. The oxygen-filled microparticle is a microcapsule containing layers of small pellets composed of lipid biomolecules, each pellet being surrounded by small bubbles of oxygen. This oxygen-filled microparticle is mainly injected into the bloodstream for functioning (see Zhang Weiwei. Rabbits without Breathing Kept Alive for 15 Minutes by Oxygen-filled Particles[N]. Science and Technology Daily, 21012-06-219(001).)

In order to overcome the limitations of oxygen supplementation methods such as ventilators and hyperbaric oxygen chambers, a negative oxygen ion generator has also been invented, such as a negative oxygen ion generator disclosed in the Chinese patent CN108539592B.

If the human body can directly absorb a large number of negative oxygen ions generated by the negative oxygen ion generator, there is an opportunity to break through the bottleneck of the current oxygen supply method limited by the conversion capacity of pulmonary alveoli of the human body. However, oxygen ions (O) are extremely unstable substances that, in the air, can easily bonded to form oxygen ($O_2$) and super oxygen ($O_3$). If the negative oxygen ions generated by the negative oxygen ion generator are released into the air, it is also impossible to detect the oxygen ions at a few centimeters away from a negative oxygen ion release port. In this way, the oxygen ions released from the negative oxygen ion generator that can be absorbed by the human body are also very limited, resulting in great limitations in allowing the human body to absorb and effectively use a sufficiently high concentration of oxygen ions to play a significant recovery and treatment effects.

SUMMARY OF THE INVENTION

An object of the present disclosure is to provide a preparation method of an oxygen capsule. The preparation method includes the following steps: treating deodorized cocoa butter liquid, which is obtained after three-stage separation, by using negative oxygen ions generated by a negative oxygen ion generator; storing ionic oxygen in the deodorized cocoa butter liquid, and then filling the deodorized cocoa butter liquid, which is treated by the negative oxygen ions and in which the ionic oxygen is stored, into a capsule shell to prepare a capsule, thereby obtaining the oxygen capsule of the present disclosure. The oxygen capsule provided by the present disclosure is high in oxygen content and has a good oxygen supplementation effect, and specifically, has a good prevention or treatment or adjuvant treatment effect on various chronic non-infectious diseases (such as hypertension, gout, gastric ulcer and anxiety disorder) as well as systemic lupus erythematosus, altitude stress, etc.

Another object of the present disclosure is to provide an application of the oxygen capsule in the preparation of a medicament or health-care food for prevention, treatment or adjuvant treatment of chronic non-infectious diseases, systemic lupus erythematosus and altitude stress.

According to an aspect of the present disclosure, a preparation method of an oxygen capsule is provided. The preparation method includes the following steps:

(1) heating deodorized cocoa butter to 50-70° C. and then cooling to 25-28° C., standing for a certain time at a temperature of 25-28° C., and then filtering and collecting liquid to obtain cocoa butter liquid A;

(2) heating the cocoa butter liquid A to 30-33° C. and then cooling to 19-21° C., standing for a certain time at a temperature of 19-21° C., and then filtering and collecting liquid to obtain cocoa butter liquid B;

(3) stirring the cocoa butter liquid B for a certain time at a temperature of 15-18° C., and then filtering and collecting a liquid to obtain a cocoa butter liquid C;

(4) placing the cocoa butter liquid C in a mixing device and then conveying negative oxygen ions to the mixing device to be mixed with the cocoa butter liquid C, and stopping conveying the negative oxygen ions when the mixing of the negative oxygen ions with the cocoa butter liquid C reach a saturated state, thereby obtaining the deodorized cocoa butter liquid treated by the negative oxygen ions, i.e., an oxygen capsule content; and (5) filling the oxygen capsule content to a capsule shell to obtain the oxygen capsule.

Compared with solid cocoa butter, the liquid cocoa butter is easier to mix with and undergo a chemical reaction with the negative oxygen ions, so as to fully absorb the negative oxygen ions and convert them into oxygen ions for storage therein. In addition, the oxygen capsule, which is prepared from the cocoa butter liquid with a single crystal structure or a crystal structure tending to be single, is higher in oxygen content. The cocoa butter has a polycrystalline characteristic. In addition, cocoa butters in different crystal forms have different melting points. Using this characteristic of the cocoa butter, it can be separated in multiple stages to obtain a cocoa butter with a single crystal structure or basically a single crystal structure. In the present disclosure, the deodorized cocoa butter liquid (i.e., the oxygen capsule content) treated by the negative oxygen ions, which is obtained in such a way that the cocoa butter liquid C obtained after the three-stage separation of the deodorized cocoa butter is mixed with and undergoes the chemical reaction with the negative oxygen ions, has an oxygen content up to 10-30% by mass.

At 5° C. or below, the oxygen ions contained in the oxygen capsule content are basically in a stable state. As the temperature rises, oxygen ions begin to be released gradually, and the higher the temperature, the faster the release speed. The oxygen ions contained in the oxygen capsule content are in a semi-stable state at room temperature. Therefore, the oxygen capsule provided by the present disclosure needs to be placed in a refrigerator for refrigerated storage.

The oxygen capsule provided by the present disclosure can be taken with water. After the oxygen capsule enters the human gastrointestinal tract, under the action of human body temperature, the oxygen ions in the oxygen capsule content begin to be released, are absorbed through the gastrointestinal mucosa to enter a circulatory system, and are delivered to organs in various parts of the body.

In the present application, the capsule shell for preparing the oxygen capsule may be any of pharmaceutical-grade or food-grade capsule shells disclosed in the prior art. In some embodiments, the capsule shell may be selected from at least one of a food-grade or pharmaceutical-grade gelatin capsule shell, glutinous rice capsule or corn capsule.

In some embodiments, the capsule shell may be a pharmaceutical-grade gelatin capsule shell.

As a more preferred embodiment, a preparation method of an oxygen capsule may include the following steps:

(1) heating deodorized cocoa butter to 50-70° C. and then cooling to 25-28° C., standing for 5-7 minutes at a temperature of 25-28° C., and then filtering and collecting liquid to obtain cocoa butter liquid A;

(2) heating the cocoa butter liquid A to 30-33° C. and then cooling to 20° C., standing for 6-8 minutes at a temperature of 20° C., and then filtering and collecting liquid to obtain cocoa butter liquid B;

(3) stirring the cocoa butter liquid B for 6-8 minutes at a temperature of 15-18° C., and then filtering and collecting liquid to obtain cocoa butter liquid C;

(4) placing the cocoa butter liquid C in a mixing tank and then conveying negative oxygen ions to the mixing tank to be mixed with the cocoa butter liquid C, and stopping conveying the negative oxygen ions when the mixing of the negative oxygen ions with the cocoa butter liquid C reaches a saturated state, thereby obtaining an oxygen capsule content; and (5) filling the oxygen capsule content to a capsule shell to obtain the oxygen capsule.

In the present disclosure, since when the negative oxygen ions are conveyed to the mixing tank and mixed with the cocoa butter liquid C, an oxidizing reaction will occur between the negative oxygen ions and the cocoa butter liquid C. This oxidizing reaction is an exothermic reaction, and thus, the temperature of the mixture and the mixing tank tends to rise and be higher than the ambient temperature. Therefore, in the process of conveying the negative oxygen ions into the cocoa butter liquid C, whether the mixing of the negative oxygen ions with the cocoa butter liquid C reaches a saturated state can be determined by judging whether the temperature of the mixture and/or the mixing tank has dropped back to be consistent or basically consistent with the ambient temperature.

Initial trial tests have proved that the oxygen capsule provided by the present disclosure can be effectively used for treatment or adjuvant treatment of chronic non-infectious diseases (such as hypertension, gout, chronic prostatitis, gastric ulcer, anxiety disorder and Alzheimer's disease), systemic lupus erythematosus, altitude stress, etc. Therefore, according to another aspect of the present disclosure, there is provided an application of the oxygen capsule in the preparation of a medicament or health-care food for prevention, treatment or adjuvant treatment of at least one of chronic non-infectious diseases, systemic lupus erythematosus and altitude stress.

Compared with the prior art, the present disclosure has the following beneficial effects:

(1) the preparation method of the oxygen capsule provided by the present disclosure is simple in process, easy to operate and implement, and wide in sources of raw materials;

(2) in the preparation process of the oxygen capsule provided by the present disclosure, only two components of deodorized cocoa butter and negative oxygen ions, and the food-grade or pharmaceutical-grade capsule shell are used as raw materials, such that the ingredients are safe; and the oxygen capsule is easy to carry and take, and high in user's medication compliance when used for the treatment or adjuvant treatment of diseases; and (3) the oxygen capsule provided by the present disclosure has a remarkable oxygen supplementation effect, and has a good treatment or adjuvant treatment effect on various chronic non-infectious diseases (such as hypertension, gout, chronic prostatitis, gastric ulcer, anxiety disorder and Alzheimer's disease) and systemic lupus erythematosus.

DETAILED DESCRIPTION OF THE INVENTION

Figure 1:
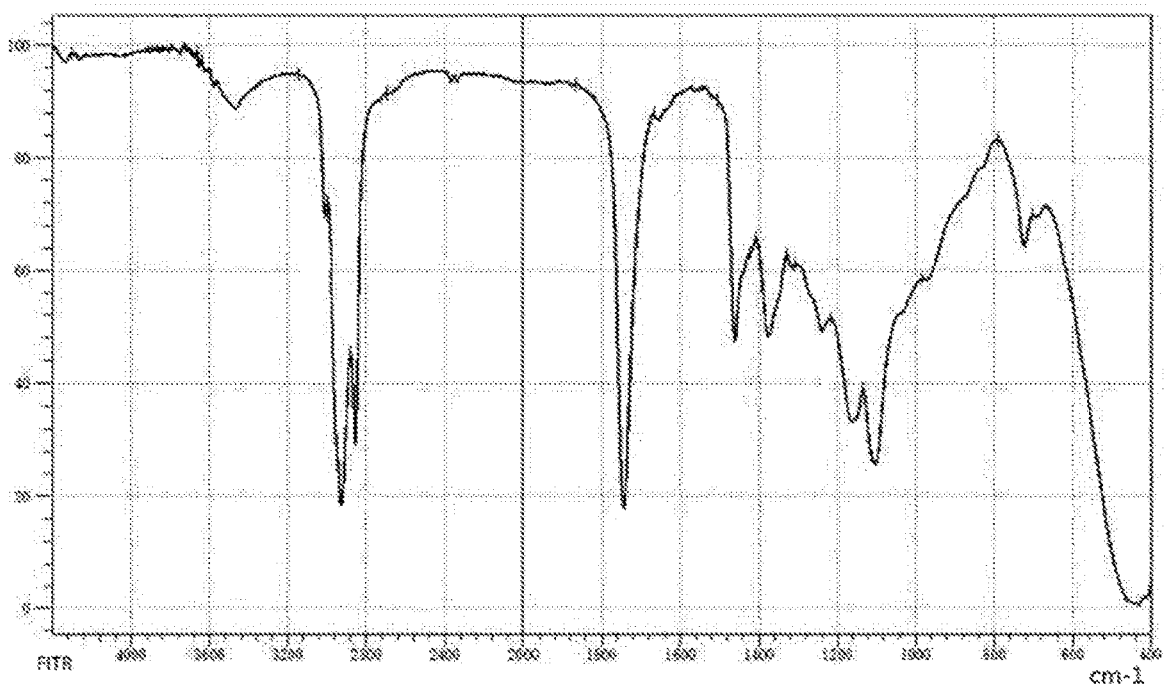
FIG. 1 is an infrared spectrogram of an oxygen capsule content of the present disclosure.

The present disclosure will be further described below in conjunction with the embodiments. Examples are used only to interpret the present disclosure, without limiting the present disclosure in any way. Unless otherwise specified, the raw materials and reagents used in the examples are conventional products that can be commercially available; and experimental methods which are not indicated with specific conditions in the examples are well-known conventional methods and conventional conditions in the art.

Example 1: Preparation Method of Oxygen Capsule

The method specifically includes the following steps:
(1) heating deodorized cocoa butter to about 50° C. while continuously stirring in the heating process such that the deodorized cocoa butter is melted sufficiently, then cooling to about 28° C., standing for about 5 minutes at a temperature of 25-28° C. and then filtering and collecting liquid to obtain cocoa butter liquid A;
(2) heating the cocoa butter liquid A to about 33° C. while stirring, then placing the resulting product in a thermostat with a temperature set to 20° C. and standing for 6 minutes, and then filtering and collecting liquid to obtain cocoa butter liquid B;
(3) placing the cocoa butter liquid B in a thermostat with a temperature set to 15° C. and continuously stirring for about 6 minutes, and then filtering and collecting liquid to obtain cocoa butter liquid C;
(4) placing the cocoa butter liquid C in a sealed mixing tank and then conveying negative oxygen ions generated by a negative oxygen ion generator to the mixing tank through an airtight pipeline, such that the negative oxygen ions are mixed with the cocoa butter liquid C; and stopping conveying the negative oxygen ions when a temperature of the mixing tank rises first and then drops back to be consistent or basically consistent with an ambient temperature, i.e., when the mixing of the negative oxygen ions with the cocoa butter liquid C reaches a saturated state, thereby obtaining an oxygen capsule content; and
(5) filling the oxygen capsule content to a pharmaceutical-grade gelatin capsule shell to obtain the oxygen capsule.

Example 2: Preparation Method of Oxygen Capsule

The method specifically includes the following steps:
(1) heating deodorized cocoa butter to about 60° C. while continuously stirring in the heating process such that the deodorized cocoa butter is melted sufficiently, then cooling to about 25° C., placing the resulting product in a thermostat with a temperature set to 25° C. and standing for about 7 minutes, and then filtering and collecting liquid to obtain cocoa butter liquid A;
(2) heating the cocoa butter liquid A to about 33° C. while stirring, then placing the resulting product in a thermostat with a temperature set to 20° C. and standing for 8 minutes, and then filtering and collecting liquid to obtain cocoa butter liquid B;
(3) placing the cocoa butter liquid B in a thermostat with a temperature set to 16° C. and continuously stirring for about 8 minutes, and then filtering and collecting liquid to obtain cocoa butter liquid C;
(4) placing the cocoa butter liquid C in a sealed mixing tank and then conveying negative oxygen ions generated by a negative oxygen ion generator to the mixing tank through an airtight pipeline, such that the negative oxygen ions are mixed with the cocoa butter liquid C: and stopping conveying the negative oxygen ions when a temperature of the mixing tank rises first and then drops back to be consistent or basically consistent with an ambient temperature, i.e., when the mixing of the negative oxygen ions with the cocoa butter liquid C reaches a saturated state, thereby obtaining an oxygen capsule content; and
(5) filling the oxygen capsule content to a pharmaceutical-grade gelatin capsule shell to obtain the oxygen capsule.

Example 3: Preparation Method of Oxygen Capsule

The method specifically includes the following steps:
(1) heating deodorized cocoa butter to about 70° C. while continuously stirring in the heating process such that the deodorized cocoa butter is melted sufficiently, then cooling to about 26° C., placing the resulting product in a thermostat with a temperature set to 25° C. and standing for about 7 minutes, and then filtering and collecting liquid to obtain cocoa butter liquid A;
(2) heating the cocoa butter liquid A to about 30° C. while stirring, then placing the resulting product in a thermostat with a temperature set to 20° C. and standing for 8 minutes, and then filtering and collecting liquid to obtain cocoa butter liquid B;
(3) placing the cocoa butter liquid B in a thermostat with a temperature set to 15° C. and continuously stirring for about 8 minutes, and then filtering and collecting liquid to obtain cocoa butter liquid C;
(4) placing the cocoa butter liquid C in a sealed mixing tank and then conveying negative oxygen ions generated by a negative oxygen ion generator to the mixing tank through an airtight pipeline, such that the negative oxygen ions are mixed with the cocoa butter liquid C; and stopping conveying the negative oxygen ions when a temperature of the mixing tank rises first and then drops back to be consistent or basically consistent with an ambient temperature, i.e., when the mixing of the negative oxygen ions with the cocoa butter liquid C reaches a saturated state, thereby obtaining an oxygen capsule content; and
(5) filling the oxygen capsule content to a pharmaceutical-grade gelatin capsule shell to obtain the oxygen capsule.

I. Component Detection for Oxygen Capsule

The oxygen capsule content prepared in Example 2 of the present disclosure was delivered to CAS Testing Technology Service (Guangzhou) Co., Ltd. in China for component detection. During the detection, a sample of the oxygen capsule content smoked when the oxygen capsule content was tried to dry under an infrared lamp. Therefore, it was also proved that the oxygen capsule content of the present disclosure contained oxygen ions and the state of the oxygen ions was unstable, and the oxygen ions would be released after heating, resulting in combustion of the sample of the oxygen capsule content at a high temperature.

Figure 2:
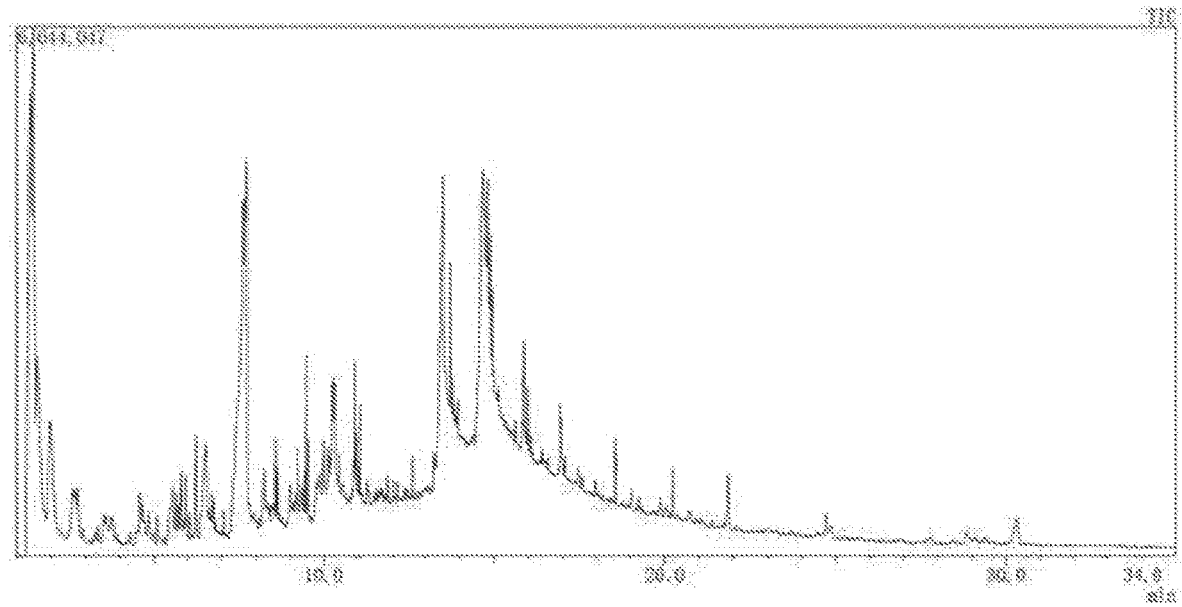
FIG. 2 is a total ion flow pattern of pyrolysis-gas chromatography-mass spectrometry (Py-GC/MS) of the oxygen capsule content of the present disclosure.
Figure 3:
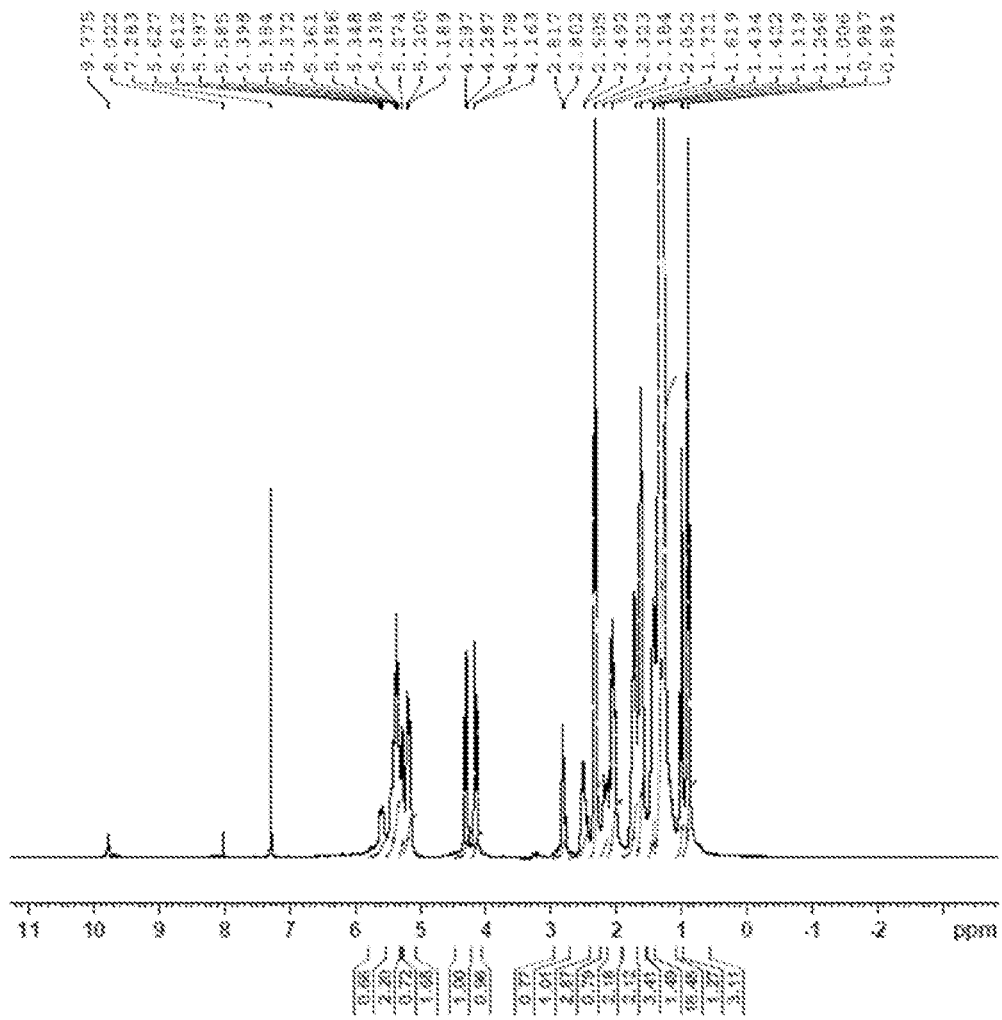
FIG. 3 is a nuclear magnetic resonance hydrogen spectrogram of the oxygen capsule content of the present disclosure.
Figure 4:
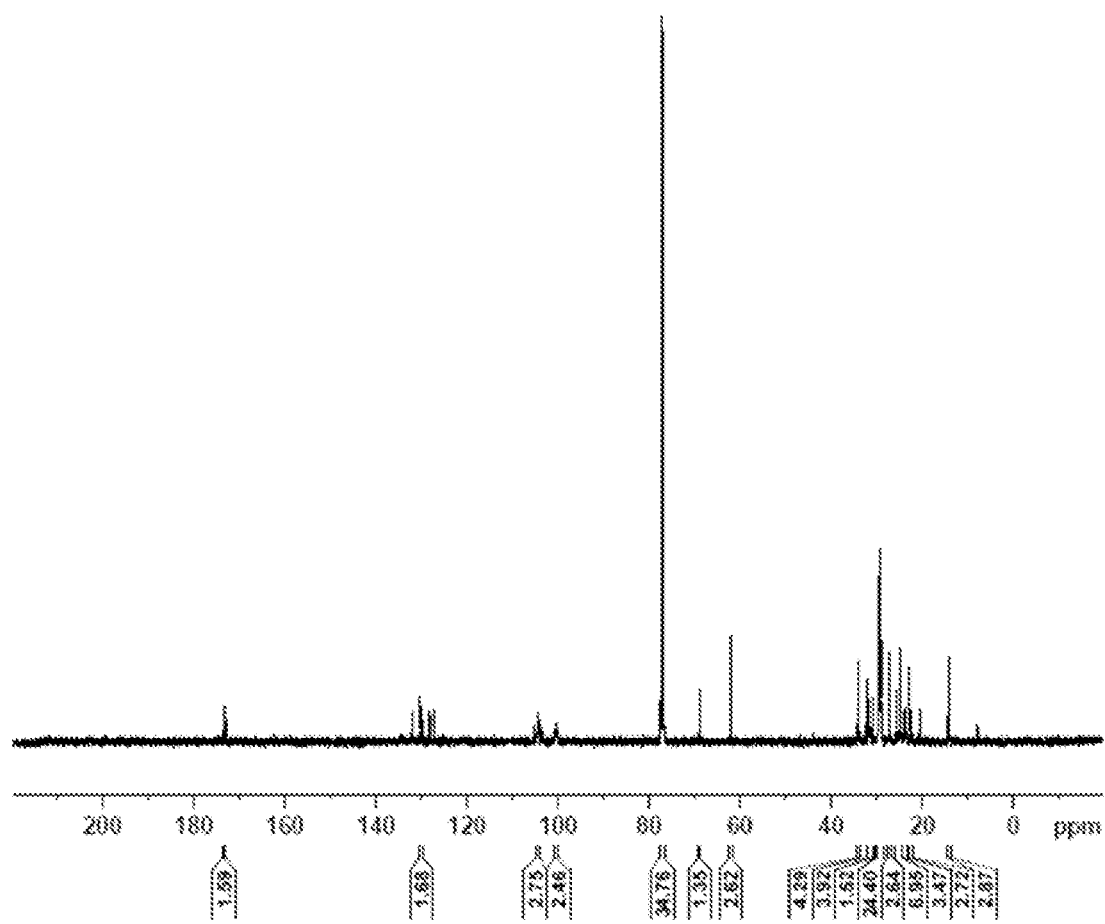
FIG. 4 is a nuclear magnetic resonance carbon spectrogram of the oxygen capsule content of the present disclosure.

An original sample of the oxygen capsule content was detected. An infrared spectrogram, a total ion flow pattern of pyrolysis-gas chromatography-mass spectrometry (Py-GC/MS), a nuclear magnetic resonance hydrogen spectrogram and a nuclear magnetic resonance carbon spectrogram of the oxygen capsule content of the present disclosure were shown in FIGS. 1-4 in turn. According to the spectrum analysis, the oxygen capsule content provided by the present disclosure mainly includes the following components: fatty acid glycerides, fatty acid isopropyl esters, fatty acids, fatty aldehydes, and fatty acid glycidyl esters.

Since the state of the oxygen ions in the oxygen capsule content was unstable and cannot be detected alone, only the oxygen content in the oxygen capsule content was detected. Upon detection, the oxygen content in the oxygen capsule content provided by the present disclosure was 24.286%. The oxygen capsule content might also contain some intermediate products that were unstable in nature, but could not be accurately separated or identified because they were easy to polymerize into polymers under detection conditions.

II. Typical Cases of Using the Oxygen Capsule of the Present Disclosure for Treatment or Adjuvant Treatment of Diseases Case I: Hypertension Ms. Zhao, aged 79 and lived in Guangzhou, had a history of hypertension for 10 years. Before taking the oxygen capsule of the present disclosure, her blood pressure was generally 140-160/110 mm/Hg. If it was higher than 140 mm/Hg before bedtime, she needed to take a piece of valsartan after she woke up the next morning. She started taking the oxygen capsule of the present disclosure in December 2018; and after taking it for 1 month, her blood pressure before going to bed never exceeded 140 mmHg, and valsartan was no longer taken since then. Now, her usual blood pressure was generally 120-140/80 mmHg.

Case II: Hypertension

Mr. Wang, aged 59 and lived in Beijing, had a history of hypertension for 7 years. Before taking the oxygen capsule of the present disclosure, his blood pressure was generally 140-150/90 mmHg, and he took antihypertensive medication every morning. He started taking the oxygen capsule orally at the end of May 2021 with two capsules per day on an empty stomach, and stopped taking the antihypertensive medication at the end of June 2021. The blood pressure was generally maintained at 115/80 mmHg at present. After one week of oral administration of the oxygen capsule, he had morning erections daily.

Case III: Gout

Mr. Zhou, aged 47 and lived in Guangzhou, had a history of gout for 5 years. Before taking the oxygen capsule of the present disclosure, his blood uric acid value was 630, and then dropped to 522 three months after starting taking the oxygen capsules in 2019. Since then, no medical measures had been taken; in 2020, the physical examination found that the blood uric acid value dropped to 347; and in July 2021, the physical examination found that the blood uric acid value was maintained at 279. It was basically meant that the gout had been cured radically.

Case IV: Gout

Mr. Wang, aged 46 and lived in Beijing, had a history of gout for 2 years. Before taking the oxygen capsule of the present disclosure, his blood uric acid value was 441. He started taking the oxygen capsule in June 2021, and did not take any other drugs during this period. In the physical examination at the end of August 2021, his blood uric acid value dropped to 411, which was in the normal blood uric acid value range.

Case V: Prostatitis, Alzheimer's Disease

Mr. Li, aged 86 and lived in Shanghai, suffered from both chronic prostatitis and Alzheimer's disease. His prostatitis was so severe that a urinary catheter was needed for urination. In September 2018, he started taking the oxygen capsule by oral or anal administration. After 3 months, his body inflammations disappeared; and 7 months later, based on a color Doppler ultrasound, the doctor decided that the urinary catheter could be removed, which would not affect his urination. The color Doppler ultrasound data before taking the oxygen capsule and 7 months after taking the oxygen capsule were shown in Table 1 below:

TABLE 1

| | | |
|---|---|---|
| Transverse diameter | 4.6 cm | 4.3 cm |
| Vertical diameter | 3.8 cm | 3.7 cm |
| Anteroposterior diameter | 3.5 cm | 3.0 cm |
| Internal gland size | 2.9 × 2.2 cm | 2.8 × 2.0 cm |

Taking the oxygen capsule also improved Mr. Li's Alzheimer's disease. Before taking the oxygen capsule, Mr. Li did not know his daughter very well, and could not control himself not to spit anything out of his mouth; whenever something in his mouth wanted to spit, he would spit it out regardless. After taking the oxygen capsule for 5 months, Mr. Li gradually became conscious and stopped spitting everywhere. After 6 months, he began to care whether his daughter was wearing warm clothes and urged her not to be too tired. After 9 months, he was identified as a non-Alzheimer patient in the admission test of a nursing home (a safety awareness test and a vegetable classification test).

Case VI: Anxiety Disorder

Mr. Sun, aged 60 and lived in North America, was a golf coach. He had a history of anxiety disorder for 5 years and usually needed to take two sleeping pills to fall asleep. He needed to take up to 4 capsules to fall asleep during a student's competition. He was suffered from the symptoms such as stomach upset, dizziness, and restlessness in a case of a little pressure. In February 2019, he took two oxygen capsules for the first time; and although he still took 2 sleeping pills that night, his sleep quality improved significantly, and he felt energetic the next day. After one month, the sleeping pills were completely discontinued at an average decrease rate of half a pill per week. Since April 2019, he has taken one oxygen capsule a day without taking any sleeping pills. Even with a pre-competition pressure, symptoms such as stomach upset, dizziness, and restlessness no longer appeared.

Case VII: Systemic Lupus Erythematosus

Ms. Zhai, aged 52 and lived in North America, was a domestic service provider. Thirty years ago, she was diagnosed with systemic lupus erythematosus, and her blood tests showed that her white blood cells, platelets and lymphocytes were significantly lower than the normal ranges. She was unable to be cured after reception of a variety of medical drug therapies (including hormonal drugs and traditional Chinese medicine). When taking hormone drugs, huge side effects on her body resulted in allergies to light and easy fatigue. She fevered almost every day, and needed to sleep for an hour or two at noon every day, otherwise would be very tired in the afternoon and evening. She started taking the oxygen capsule in 2018. Before taking the oxygen capsule (Jun. 5, 2017), blood tests were done in the United States, and results of several blood phase indicators related to systemic lupus erythematosus were shown in Table 2:

TABLE 2

| Checklist | Results | Normal ranges |
| --- | --- | --- |
| White blood cells WBC | 2.1 | 4.5-10.8 |
| Platelets PLT | 101 | 130-400 |
| Lymphocyte LYM # | 0.5 | 1.2-3.4 |

After taking the oxygen capsule for half a year, she stopped having a fever, and no sleep at all during the day. She felted vigorous all day. After taking the oxygen capsule for more than two years, she was examined at the First Affiliated Hospital of Sun Yat-sen University in Guangzhou, China, and results of the several blood phase indicators related to systemic lupus erythematosus were shown in Table 3:

TABLE 3

| Checklist | Results | Normal ranges |
| --- | --- | --- |
| White blood cells WBC | 3.21 | 4-10 |
| Platelets PLT | 125 | 100-300 |
| Lymphocyte LYM # | 1.0 | 1.0-3.3 |

The value of the white blood cells was near a normal value, and the values of the platelets and lymphocytes were already normal.

Case VIII: Gastric Ulcer

Mr. Lin, aged 29 and lived in Guangdong, had a history of gastric ulcer for 6 years. He had to eat on time, or suffered from unbearable gastric colic. Since March 2020, he has taken oxygen capsules, two capsules per day, for a total of 20 days, during which he did not take any other drugs; and after hospital examination, the stomach ulcer wound healed, and no more stomach pain occurred after that.

The foregoing is merely some of the embodiments of the present disclosure. For those of ordinary skill in the art, without departing from the concept of the present disclosure, several modifications and improvements can also be made, and these all fall within the protection scope of the present disclosure.

What is claimed is:

1. A preparation method of an oxygen capsule, comprising the following steps:
   (1) heating deodorized cocoa butter to 50-70° C. and then cooling to 25-28° C., standing for 5-7 minutes at a temperature of 25-28° C., and then filtering and collecting liquid to obtain cocoa butter liquid A;
   (2) heating the cocoa butter liquid A to 30-33° C. and then cooling to 20° C., standing for 6-8 minutes at a temperature of 20° C., and then filtering and collecting liquid to obtain cocoa butter liquid B;
   (3) stirring the cocoa butter liquid B for 6-8 minutes at a temperature of 15-18° C., and then filtering and collecting liquid to obtain cocoa butter liquid C;
   (4) placing the cocoa butter liquid C in a mixing tank and then conveying negative oxygen ions to the mixing tank to be mixed with the cocoa butter liquid C, and stopping conveying the negative oxygen ions when the mixing of the negative oxygen ions with the cocoa butter liquid C reaches a saturated state, thereby obtaining an oxygen capsule content; and
   (5) filling the oxygen capsule content to a pharmaceutical or food grade capsule shell to obtain the oxygen capsule;
   wherein an oxygen content of the oxygen capsule is 10-30% by mass.

2. The preparation method according to claim 1, wherein the capsule shell is selected from at least one of a gelatin capsule shell, a glutinous rice capsule shell, and a corn capsule shell.

3. The preparation method according to claim 1, wherein the capsule shell is the gelatin capsule shell.

* * * * *